United States Patent [19]

Devine

[11] Patent Number: 5,697,898

[45] Date of Patent: Dec. 16, 1997

[54] AUTOMATED FREE FLOW MECHANISM FOR USE IN PHACOEMULSIFICATION, IRRIGATION AND ASPIRATION OF THE EYE

[75] Inventor: Terence M. Devine, Athens, Pa.

[73] Assignee: Surgical Design Corporation, Long Island City, N.Y.

[21] Appl. No.: 658,816

[22] Filed: May 31, 1996

[51] Int. Cl.$^6$ .................................................. A61B 17/20
[52] U.S. Cl. ................................................ 604/22; 606/169
[58] Field of Search ............................... 604/20, 22, 117, 604/118; 606/108, 159, 166, 32, 169

[56] References Cited

U.S. PATENT DOCUMENTS

| | | | |
|---|---|---|---|
| 4,428,748 | 1/1984 | Peyman et al. ........................ | 604/22 |
| 4,465,470 | 8/1984 | Kelman . | |
| 4,737,148 | 4/1988 | Blake . | |
| 4,921,477 | 5/1990 | Davis ..................................... | 604/22 |
| 4,922,902 | 5/1990 | Wuchinich et al. . | |
| 5,062,827 | 11/1991 | Wiksell ................................... | 604/22 |
| 5,154,696 | 10/1992 | Shearing . | |
| 5,242,385 | 9/1993 | Strukel . | |
| 5,328,456 | 7/1994 | Horiguchi et al. ...................... | 604/22 |
| 5,334,183 | 8/1994 | Wuchinich . | |
| 5,370,652 | 12/1994 | Kellan . | |
| 5,403,276 | 4/1995 | Schechter et al. ..................... | 604/22 |

FOREIGN PATENT DOCUMENTS 8607249  12/1986  WIPO ..................................... 604/22

OTHER PUBLICATIONS

"How to Set the Dials", Terence M. Devine, M.D.

*Primary Examiner*—William Lewis
*Attorney, Agent, or Firm*—Darby & Darby

[57] ABSTRACT

An apparatus and method for removing a cataract lens from an eye, the apparatus comprising a surgical handpiece capable of phacoemulsification, irrigation and aspiration, for insertion into the eye, an infusion reservoir containing infusion fluid, the infusion reservoir being connected to the surgical handpiece by an infusion line, an evacuation line having a first end connected to the surgical handpiece and a second end which lead to a collection container, and a free flow valve, located along the evacuation line, for controlling the flow of fluid through the evacuation line, wherein the infusion reservoir is placed above the level of the eye and the level of the evacuation line so that, when the free flow valve is in the open position, infusion fluid is permitted to flow from the infusion reservoir into the eye, through the evacuation line and into the collection container.

48 Claims, 7 Drawing Sheets

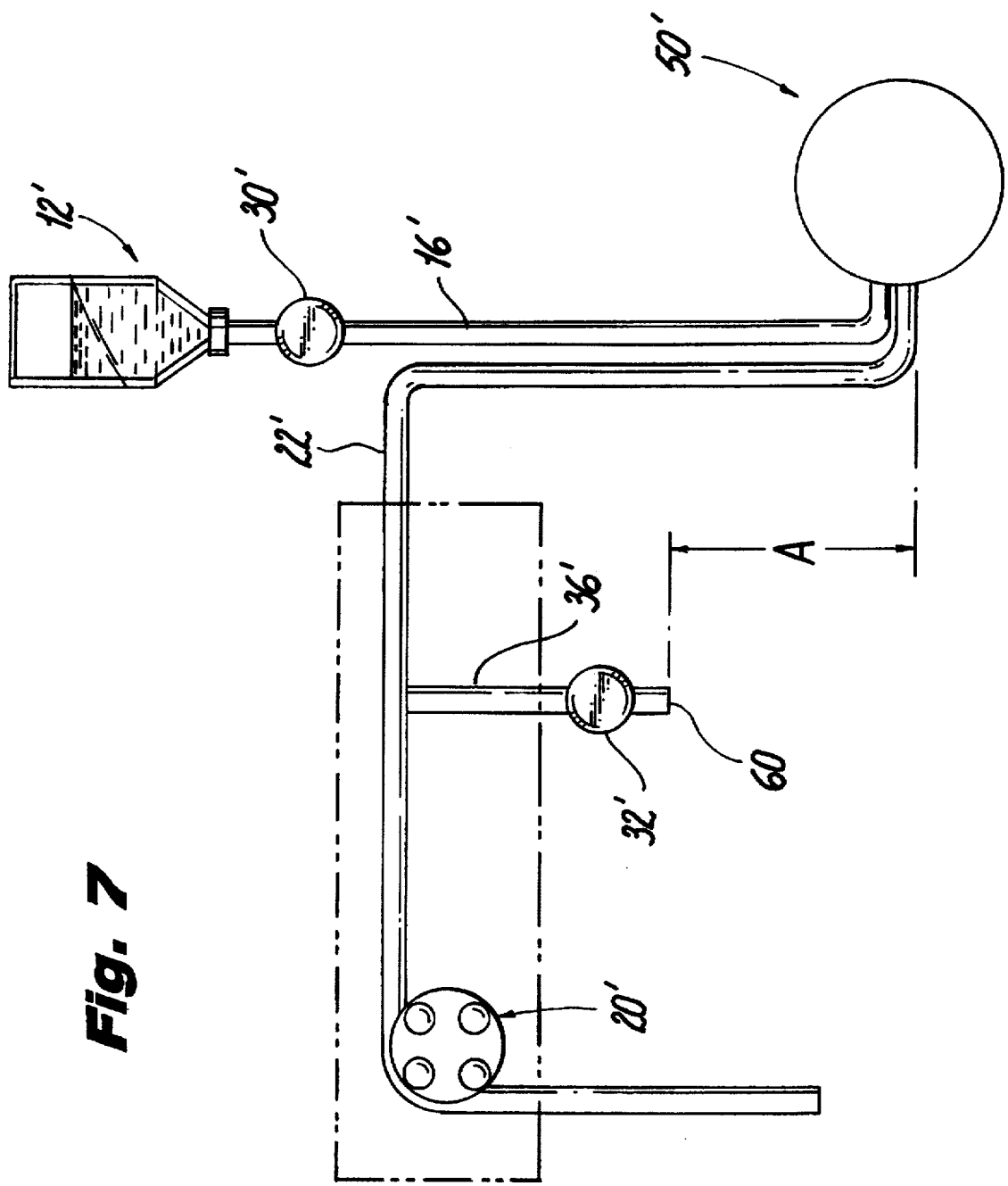

AUTOMATED FREE FLOW MECHANISM FOR USE IN PHACOEMULSIFICATION, IRRIGATION AND ASPIRATION OF THE EYE

BACKGROUND OF THE INVENTION

This invention relates to an automated free flow mechanism to be used in conjunction with phacoemulsification, irrigation and aspiration systems and, more particularly, to a free flow valve positioned within the evacuation line so that fluid and cataract particles may be removed from the eye without the use of a vacuum to draw fluid through the eye.

Phacoemulsification is a well known surgical procedure which uses ultrasonic energy to breakup and remove the nucleus of a cataract. The nucleus of the cataract is anatomically subdivided into zones including: (1) cortex-soft young lens fibers which lie directly beneath the lens capsule; and (2) the nuclei, subdivided into the embryonic nucleus, the fetal nucleus, the infantile nucleus, and the adult nucleus. Surgically, the nucleus can be separated into two zones: (1) the denser central nucleus; and (2) the softer outer epinucleus which lies closest to the lens capsule, by injecting fluid between them via a process called hydrodelineation or hydrodelamination. The central nucleus may then be removed using the phacoemulsification process while the epinucleus maintains a protective barrier between the phaco ultrasonic instrument tip and the delicate lens capsule. Subsequent removal of the epinucleus poses a greater potential for rupturing the delicate posterior lens capsule. With conventional machines employing a vacuum source, the ultrasonic power is always engaged with vacuum to create how and maintain "hold" on the lens material. When working to remove the soft, relatively thin epinucleus, this combination of ultrasonic power and vacuum can produce sudden unpredictable penetration of the epinucleus and concomitant rupture of the lens capsule. This could then create vitreous loss and its associated risks, including retinal detachment and Cystoid Macular Edema ("CME"). Vitreous loss is associated with increased risks including retinal detachment and, therefore, is undesirable. Further, any remaining nucleus particles can be dispersed into the vitreous cavity 53 and may require a second surgical procedure to remove them.

Therefore, it remains important that the intraocular pressure remains nearly constant. Where a vacuum pump is used to draw fluid from the eye, a constant pressure is achieved by keeping the rate of the fluid flow from the eye equal to the fluid being drawn into the eye from the infusion reservoir. However, if the evacuation port becomes occluded by, for example, cataract material, a pressure differential is created with positive pressure occurring inside the eye and negative pressure (vacuum) occurring inside the handpiece and/or evacuation line. Unless relieved, this pressure differential will increase as the pump continues to generate vacuum. When the occluding material is eventually sucked into the evacuation tube, the sudden rush of fluid and/or sucking forces may cause the above-identified damage to the eye.

It is, therefore, an object of the invention to provide a mechanism for achieving phacoemulsification, irrigation and aspiration of the eye without the potentially hazardous effects of using vacuum to draw the fluid through the eye.

It is further an object of the invention to provide enhanced protection against fluid surge which occurs from the increasing pressure differential across the occluded evacuation port.

SUMMARY OF THE INVENTION

The present invention is directed to an automated free flow mechanism to be used in conjunction with phacoemulsification machines for removing cataract material, for example, nucleus, epinucleus, cortex and lens capsule fibers, plaque and debris, from the inside of the eye. The automated free flow mechanism does not employ a vacuum to create the flow of fluid out of the eye, thereby avoiding all of the potential hazards associated therewith.

In an illustrative embodiment of the invention, a phacoemulsification machine comprising a surgical handpiece for inserting into the eye of a patient is connected to both an infusion reservoir and, typically, a vacuum pump. According to the invention, phacoemulsification and aspiration and irrigation of the cataract is carried out via an "automated free flow mechanism" ("AFF") which utilizes a free flow valve, designed to allow the free flow of fluid from the infusion reservoir into the eye, through the evacuation port of the handpiece and the evacuation tubing, and into a collection container. The AFF utilizes the positive pressure, created by placing the infusion bottle at a higher position relative to the evacuation line, to create a flow of material from within the eye through the evacuation port of the handpiece.

Although no vacuum pressure is required to cause this fluid flow out of the eye, vacuum pumps may still be used where the surgeon requires accelerated removal of cataract material once the material is maneuvered safely away from the delicate lens capsule within the eye. In such a situation, the free flow valve provides enhanced surge protection.

BRIEF DESCRIPTION OF THE DRAWINGS

The foregoing and other features of the present invention will be more readily apparent from the following detailed description and drawings of illustrative embodiments of the invention in which:

FIG. 7 illustrates a possible modification of an automated free flow mechanism according to the present invention.

DETAILED DESCRIPTION OF ILLUSTRATIVE EMBODIMENTS

Figure 1:
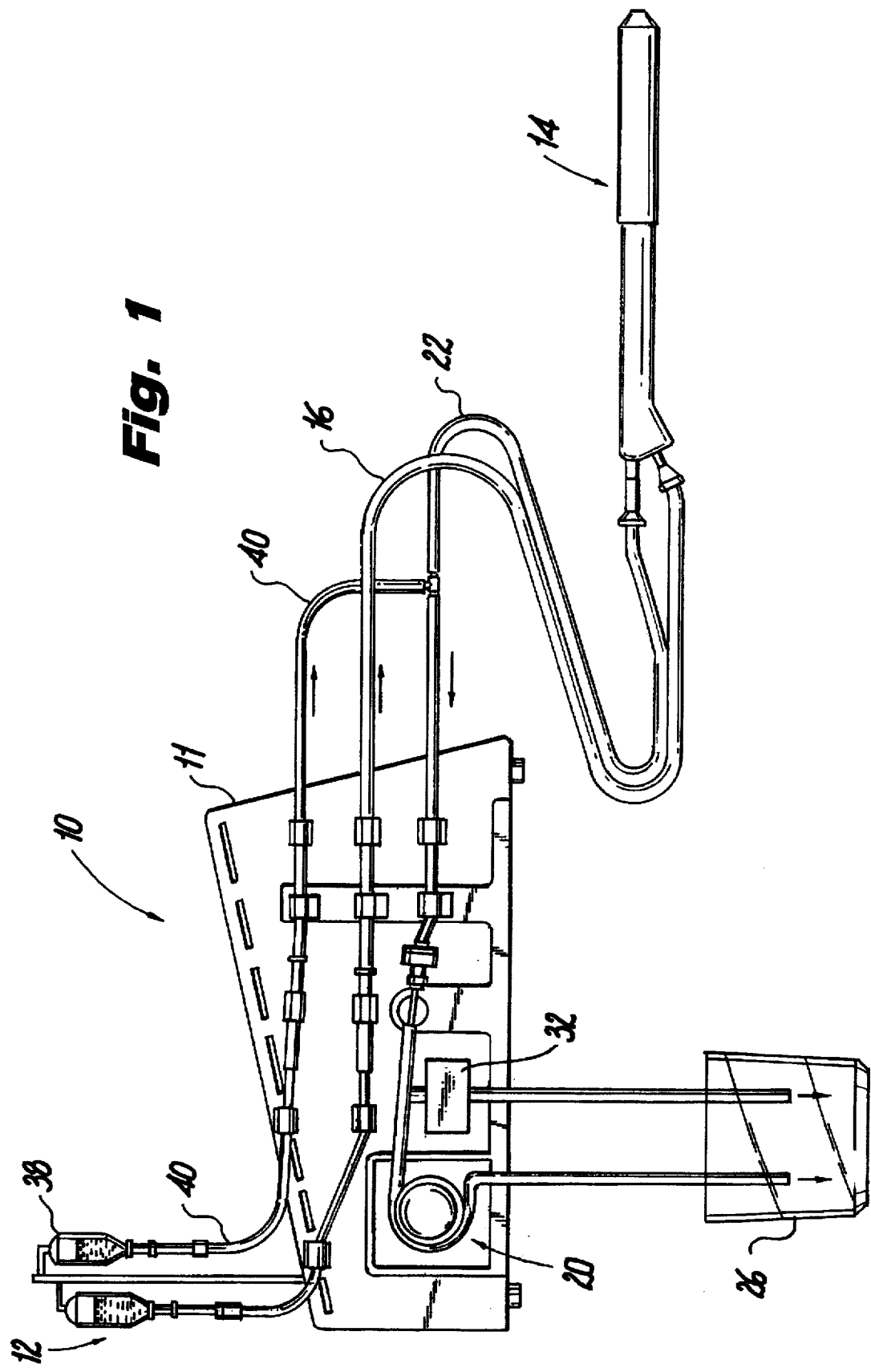
FIG. 1 is an illustrative embodiment of an automated free flow mechanism according to the invention, as used in conjunction with a phacoemulsification machine.

FIG. 1 illustrates a phacoemulsification machine 10, used for cataract surgery on either humans or animals, according to the invention. The phacoemulsification machine 10, operating on the principle of fluid flow into and out of an eye 50 (FIG. 2), comprises an infusion reservoir 12 containing infusion fluid, which is connected to a surgical handpiece 14 via an infusion line 16, and a vacuum pump 20 connected to the surgical handpiece 14 by an evacuation line 22. For purposes of illustration, the infusion and evacuation lines are shown as entering the eye through two separate incisions. While this arrangement may be used, it is preferable to have the infusion line enter the eye through the same handpiece as the evacuation line. Typically, the infusion line and evacuation line are coaxial, with the infusion line being annular in cross-section and disposed about the evacuation line.

The infusion and evacuation lines (16 and 22) are preferably made from surgical tubing. The inflow or infusion originates from the infusion reservoir 12 and is carried to the eye 50 through the infusion line 16. This infusion fluid exits the eye 50 through an evacuation port 24 located, typically, at the tip of a surgical handpiece 14, through the evacuation line 22, and is deposited into a collection container 26. The vacuum pump 20 may be activated to provide suction for removing fluid and cataract particles from the eye 50. Although a peristaltic pump is illustrated in FIG. 1, any suitable vacuum pump, for example, a venturi or a diaphragm pump may be used. (See FIGS. 4A and 4B.)

In accordance with conventional practice, an ultrasonic handpiece (not shown) may be used first to emulsify the cataract material. After the material is emulsified, the ultrasonic handpiece is replaced by an irrigation/aspiration ("I/A") handpiece 14.

Figure 2:
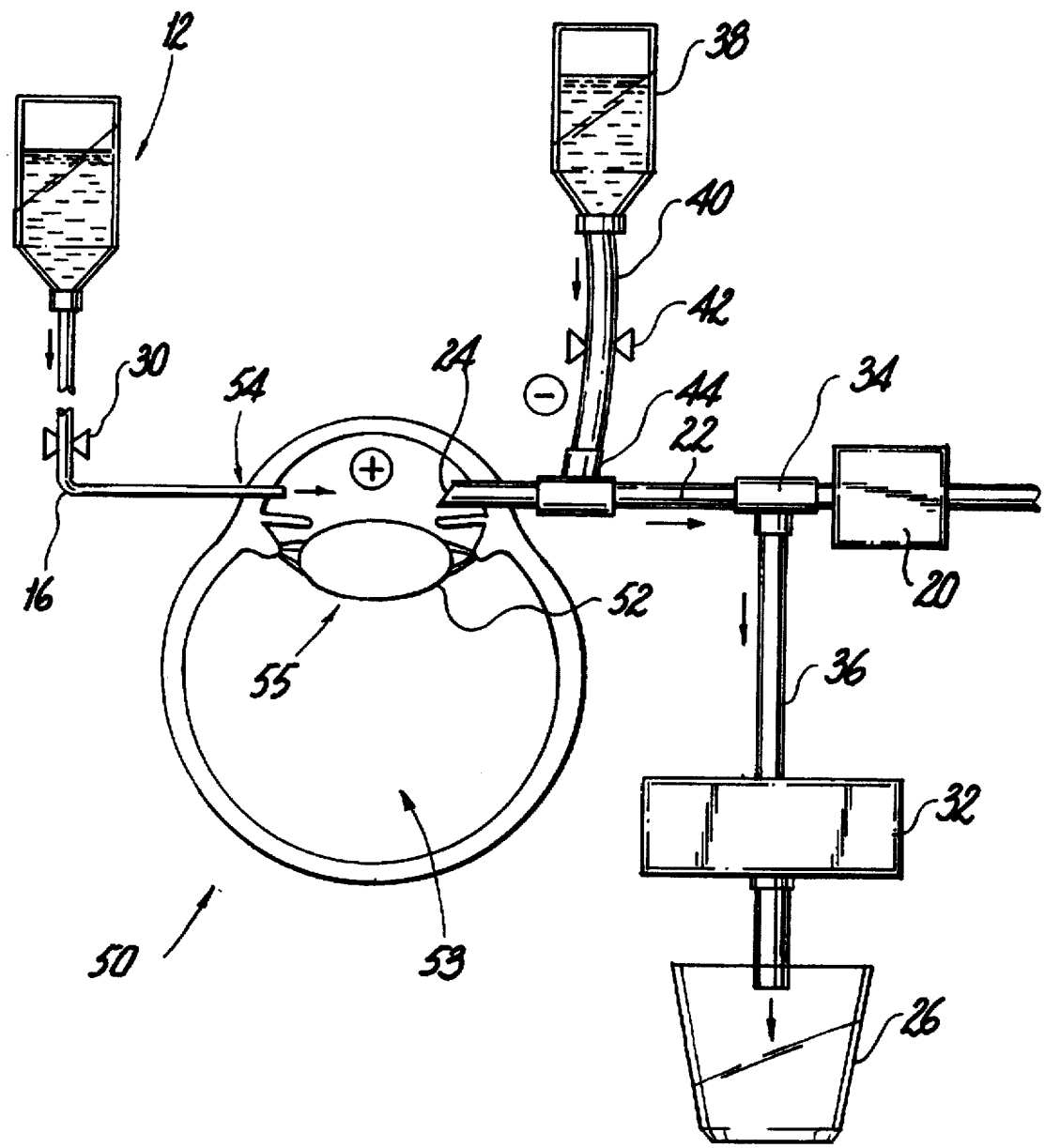
FIG. 2 is a simplified sketch of a phacoemulsification, irrigation and aspiration system, employing the automated free flow mechanism.

As shown in FIG. 2, an infusion valve 30 is attached to the infusion line 16 to control the flow of infusion fluid therethrough. Any suitable valve may be used, for example, a mechanical or solenoid-operated pinch valve. According to the invention, a free flow valve 32 is inserted within the evacuation line 22 between the eye 50 and the vacuum pump 20. By controlling these valves, the flow into and out of the eye 50 may be controlled. Although FIG. 1 shows the free flow valve 32 attached to the phacoemulsification machine console 11, the free flow valve 32 may be conveniently positioned anywhere along the evacuation line 22 between the eye 50 and the vacuum pump 20 or as a modification of a collection container (FIG. 4B). This free flow valve 32 is designed to remove fluid and cataract particles without the use of vacuum pressure via a phenomenum referred to herein as "Automated Free Flow" (AFF). The AFF concept uses the positive fluid pressure created by the relative "high" position of the infusion reservoir 12 compared to the relative "low" position of the eye 50, the surgical hand piece 14, the evacuation line 22, and the free flow valve 32. The amount of positive pressure is controlled by adjusting the height of the infusion reservoir 12 above the patient's eye level.

FIG. 2 illustrates a simplified diagram of the phacoemulsification machine 10 containing the free flow valve 32. Its operation will first be described in the context of "capsule polishing" where the phacoemulsification machine 10 is used to remove particles from the surface of the lens capsule 52. The capsule polishing process does not involve using ultrasonic power to emulsify cataract material within the eye. As shown in FIG. 2, the lens capsule 52 is a clear elastic membrane which completely encloses the cataract lens. The lens capsule 52 is thinnest and, therefore, most delicate at its posterior pole 55. During cataract surgery, the posterior lens capsule 52 must be cleaned of cataract fiber and plaque to provide a successful visual outcome. This is done by either mechanically scraping the lens capsule 52 with curettes and various sand blasted cannulas, or by vacuuming the lens capsule 52 with an I/A handpiece 14. This latter approach uses the vacuum pump 20 on the phacoemulsification machine 10 to create low levels of vacuum pressure which, in turn, causes fluid to flow from the infusion reservoir 12, through the inside of the eye 50, and into the evacuation port 24 located at the I/A handpiece tip. The I/A handpiece tip is maneuvered over the posterior lens capsule 52, thereby vacuuming the lens capsule 52. If the lens capsule 52 is too flaccid, or if too much vacuum is created, the lens capsule 52 can be aspirated into the handpiece evacuation port 24, thereby occluding the evacuation port 24. When this occurs, a pressure differential is created across the aspirated lens capsule 52, with a positive pressure outside the tip (within the eye 50) and a negative pressure or vacuum inside the tip. Unless relieved, this pressure differential will increase as the vacuum pump 20 continues to generate vacuum. This would eventually cause the lens capsule 52 to tear, resulting in the disruption of the vitreous 53 or "vitreous loss." Vitreous loss is associated with increased risks including retinal detachment and Cystoid Macular Edema ("CME") and, therefore, is undesirable.

According to the invention, the lens capsule polishing described above is performed entirely with positive fluid pressure created by the relative placement of the infusion reservoir 12 with respect to the evacuation line 22. No vacuum is used to create the fluid flow. Hence, the risks associated with vacuum are completely avoided. As shown in FIG. 2, the free flow valve 32 is positioned within the evacuation line 22 between the vacuum pump 20 and the eye 50. Preferably, a "T" connector is inserted into the evacuation line 22, and a free flow line 36 containing the free flow valve 32 is attached to the "T" connector 34. The free flow valve 32 may be, for example, a mechanical or solenoid-operated pinch valve, and would be activated by the surgeon as desired.

In operation, the surgeon selects the AFF mode on the phacoemulsification machine console 11 (FIG. 1). This causes the machine computer logic to automatically shut down the vacuum pump 20 and permits the surgeon to open the free flow valve 32 with a surgeon controlled foot pedal (not shown). When the free flow valve 32 is opened, a fluid evacuation path is created from the eye 50, through the I/A handpiece 14 and evacuation line 22, and into the collection container 26. As designed, the evacuation path is lower than the infusion reservoir 12 to create a positive pressure differential between the infusion reservoir 12 and the evacuation line 22. By not using vacuum pressure, a safer and more predictable removal process is created.

Figure 5:
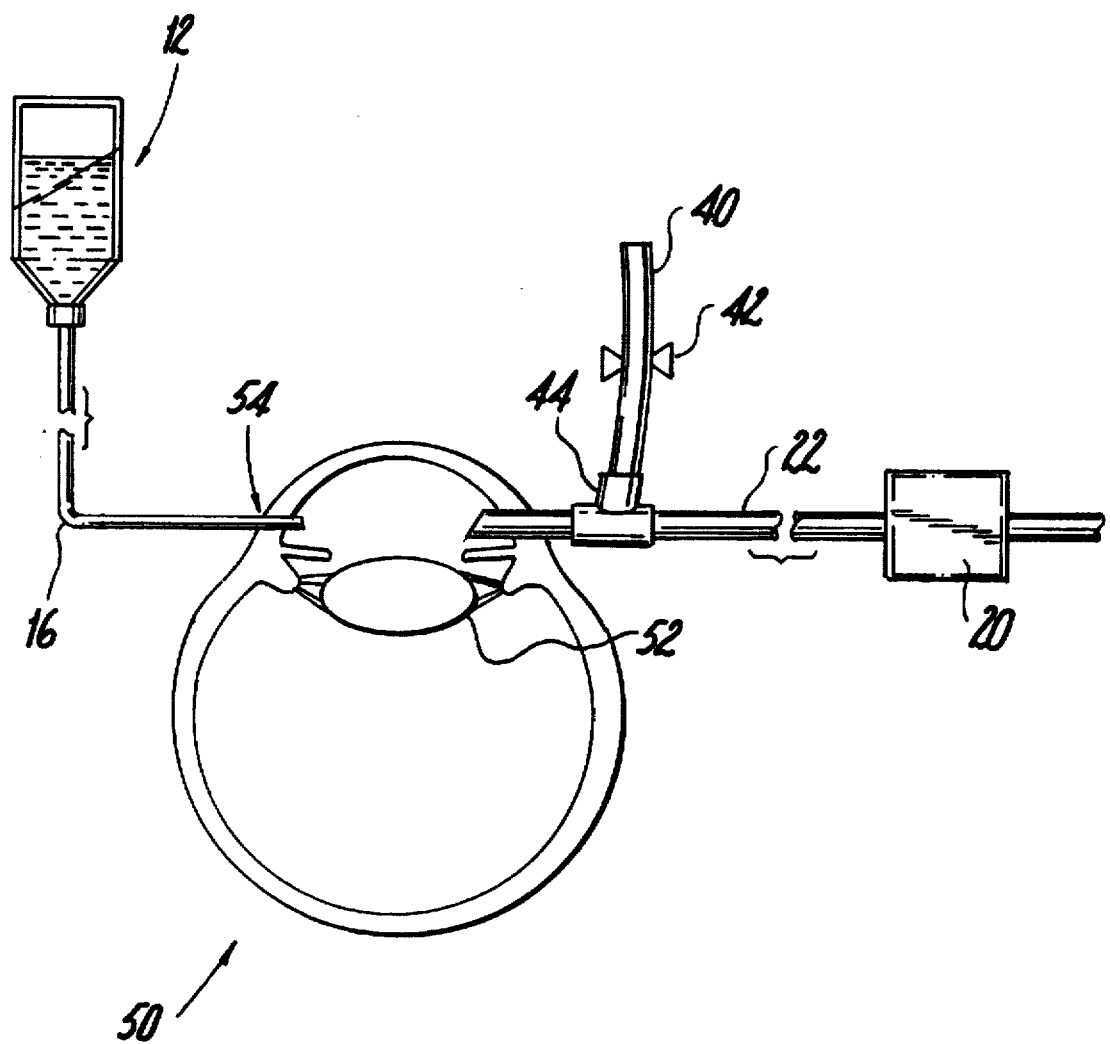
FIG. 5 illustrates the conventional surge protection mechanism for venting the evacuation line to the atmosphere.

A venting fluid reservoir 38 is also shown in FIG. 2. This venting fluid reservoir 3, connected to a venting line 40 (also known as a third line), is attached to the evacuation line 22 via a "T" connector 44. A vent valve 42 is located along the venting line 40 to open and close the venting line 40. The venting mechanism may involve either a fluid reservoir 38 (FIG. 2) or atmospheric air (FIG. 5), and allows the surgeon to reduce or neutralize vacuum in the handpiece 14 and evacuation line 22. As with the infusion valve 30 and the free flow valve 32, the vent valve 42 is preferably a mechanical or solenoid-activated pinch valve.

Preferably, the surgeon uses a multiple-position foot switch to control the status (open or closed) of the infusion valve 30 located on the infusion line 16, the free flow valve 32 located on the free flow line 36, and the vent valve 42 located on the vent line 40, as well as to activate the vacuum pump 20. By moving the foot switch to a first position (position 1), the surgeon causes the infusion valve 30 to open while keeping the vent valve and the free flow valve 32 closed, and the vacuum pump 20 off. This creates positive pressure within the eye 50 with no outflow except for leakage at the incision 54 (FIG. 2). When the foot switch is moved to position 2, the infusion valve 30 remains open and the free flow valve 32 opens. The vent valve 42 remains closed and the vacuum pump 20 remains off. This condition allows outflow through the I/A handpiece 14, the evacuation line 22, the free flow line 36, and into the collection container 26. The evacuation port 24 may now be maneuvered across the posterior lens capsule 52, thereby removing any remaining lens particles, for example, lens debris, cortex filaments and plaque. Once the lens capsule 52 has been polished, the surgeon may return the foot switch to the first (1) position. By so doing, the vent valve 42 is activated (opened) which vents fluid from the venting reservoir 38 located at a higher location than the infusion reservoir 12. The higher relative location of the venting reservoir 38 creates a reverse pressure differential; the pressure inside the handpiece 14 becomes more positive than the pressure inside the eye 50. By reversing the pressure, the fluid flow through the evacuation port of the handpiece 14 is reversed. The phacoemulsification machine may be configured so that the vent valve 42 is opened automatically whenever the surgeon places the foot switch from a higher into a lower foot switch position, for example, from foot switch position 2 to 1. The vent valve 42 may also be controlled as a separate foot pedal position.

During the capsule polishing procedure, the lens capsule 52 is held in apposition to the port by the small pressure differential created by the difference in height of the infusion fluid compared to the evacuation fluid, i.e. the fluid pressure is slightly more positive outside the evacuation port 24 (within the eye 50 as shown in FIG. 2) than inside the handpiece 14. At no time is vacuum created within the handpiece 14. Therefore, if the lens capsule 52 occludes the evacuation port 24, the pressure remains constant within the handpiece (i.e., within the evacuation line) because no mechanical pumping or vacuum generation is occurring in this conduit. When the item causing the occlusion is removed from the evacuation port 24, there will be no surge of fluid from within the eye 50 into the evacuation line. Therefore, a more predictable removal of the epinucleus shell, with a lower chance of inadvertently puncturing through the thin epinucleus and tearing the posterior lens capsule 52, results by the structure of the present invention. In other words, the risk that the lens capsule 52 will be torn by an increase of vacuum pressure in the evacuation line is removed by the present invention.

During the capsule polishing procedure, the foot switch may also be moved into a third foot switch position (position 3) which, in this example, activates the vacuum pump 20 and, simultaneously, close the free flow valve 32. Activating the vacuum pump 20 provides low levels of flow and vacuum as an adjunct to removing larger particles, and would, preferably, be used whenever the evacuation port 24 on the I/A handpiece 14 is safely positioned away from the posterior lens capsule 52.

The AFF phacoemulsification process, according to the invention, differs slightly from the above-described AFF capsule vacuuming process. In general, phacoemulsification involves using an ultrasonic handpiece to ultrasonically vibrate the tip member thereof. This process disintegrates the hard nuclear material of a cataract lens. Once the cataract lens has been broken down or emulsified, the ultrasonic handpiece is replaced by an I/A handpiece, connected to both an infusion reservoir and a vacuum pump. The I/A handpiece is then used for irrigating and aspirating fluid in the eye, thereby removing the soft cataract material from the eye. This irrigating and aspirating process is similar to that described for the AFF capsule vacuuming mode, where the pressure differential between the infusion reservoir 12 and the evacuation line 22 causes positive fluid flow through the eye 50, into the evacuation port 24 located at the tip of the I/A handpiece 14, through the evacuation line 22, and finally into the collection container 26.

To perform the AFF phacoemulsification process, the surgeon selects the AFF phacoemulsification mode on the machine console 11 and once again controls its functions with the multi-position surgeon foot pedal (not shown). As before, various combinations of foot pedal functionality can be programmed into the machine console 11, to correspond to either the manufacturer's or the surgeon's preference. Thus, the foot positions may vary from the capsule vacuuming procedure to take into account the ultrasonic handpiece and any other preferences the surgeon may have. For example, when the surgeon places the foot switch into a first position, the infusion valve 30 and the free flow valve 32 are opened, the vent valve 42 is closed, the vacuum pump remains off, and no phacoemulsification power is supplied to the ultrasonic handpiece. With the foot switch in position 1, gravity causes fluid flow through the eye. When the foot switch is moved into a second foot switch position (position 2), power is now supplied to the ultrasonic handpiece to emulsify any cataract material within the eye.

During the AFF phacoemulsification procedure, the phacoemulsification machine may also be configured with a third foot switch position, wherein the infusion valve 30 remains open, the free flow valve 32 is closed, the vent valve 42 is open, the ultrasonic power remains on, and the vacuum pump is turned on. This mode provides the surgeon with the option to use vacuum pressure to, for example, speed up the phacoemulsification process. As before, this mode would preferably be used when the handpiece 14 is safely positioned away from the posterior lens capsule 52. Also, the phacoemulsification machine may be configured so that the vent valve 42 is opened automatically whenever the surgeon moves from a higher to a lower foot switch position. By opening the vent valve 42, the fluid flow through the eye would be reversed, thereby removing any lens material which may be causing an occlusion at the evacuation port 24. The vent valve 42 may also be opened whenever the surgeon so desires, for example, to "unclog" an occlusion at the evacuation port 24. This is especially true when the venting line is connected to fluid reservoir 38, which is disposed above infusion reservoir 12.

During the AFF phacoemulsification procedure, when the ultrasonic handpiece is actuated, the vibrating needle will convey fluid from the eye into the evacuation line. Therefore, the ultrasonic handpiece will assist either the vacuum pump and/or the gravity flow from the infusion reservoir. The ultrasonic handpiece can incorporate a needle such as those disclosed in U.S. Pat. No. 5,242,385 to Strukel, the disclosure of which is hereby incorporated by reference. Alternatively, the needles disclosed in Applicant's currently pending application Ser. No. 08/458,409, the disclosure of which is hereby incorporated by reference, may be used. Applicants believe that the internal stepped diameters of the needle tip helps assist, when the needle is vibrating, in evacuating fluid from within the eye into the evacuation line. However, the present inventor has also seen fluid being assisted in evacuating from within the eye with a vibrating needle tip that has a constant internal diameter.

In both the AFF capsule vacuuming AFF phacoemulsification modes, audible signals consisting of different tones and patterns, for example, beeps, drips, and whistles, can be selected to differentiate various foot pedal positions for the surgeon. Also, the ultrasonic power may be predetermined in terms of percentage of stroke amplitude (power) and in terms of pulse modality. For example, 30 percent power with a pulser ultrasonic power mode set to a rate of 6 (6 cycles per minute) could be programmed as a specific console setting or control button with a specific label indicating its use for free flow removal of the epinuclear shell. Another option would be to allow the surgeon to select these parameters (power, pulse) independently.

Figure 3A:
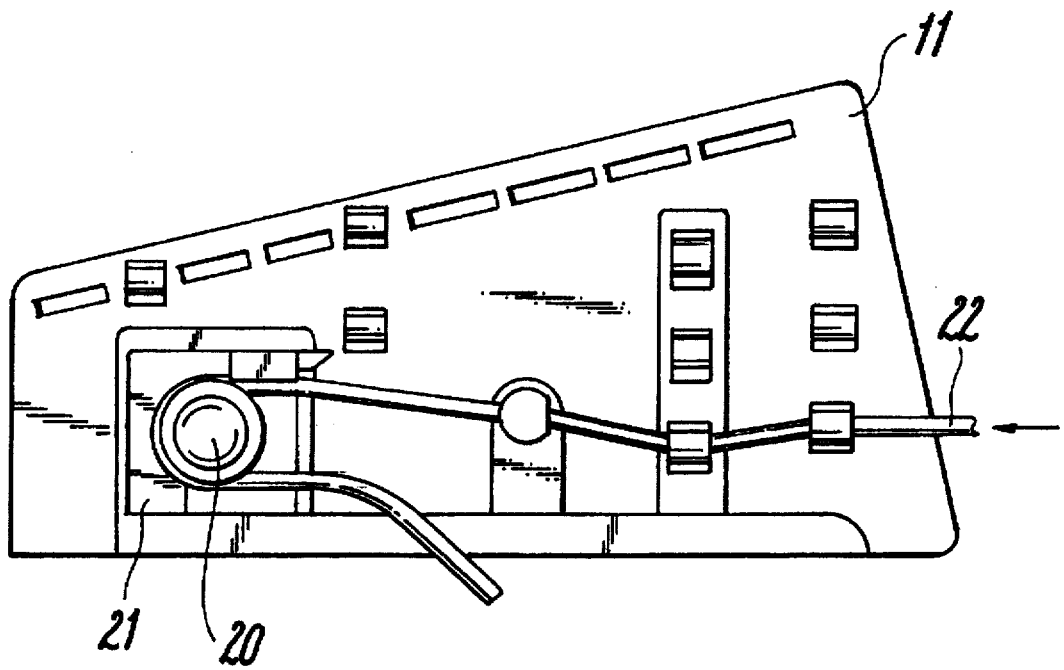
FIGS. 3A and 3B illustrate the modification of a peristaltic vacuum pump according to the invention.
Figure 3B:
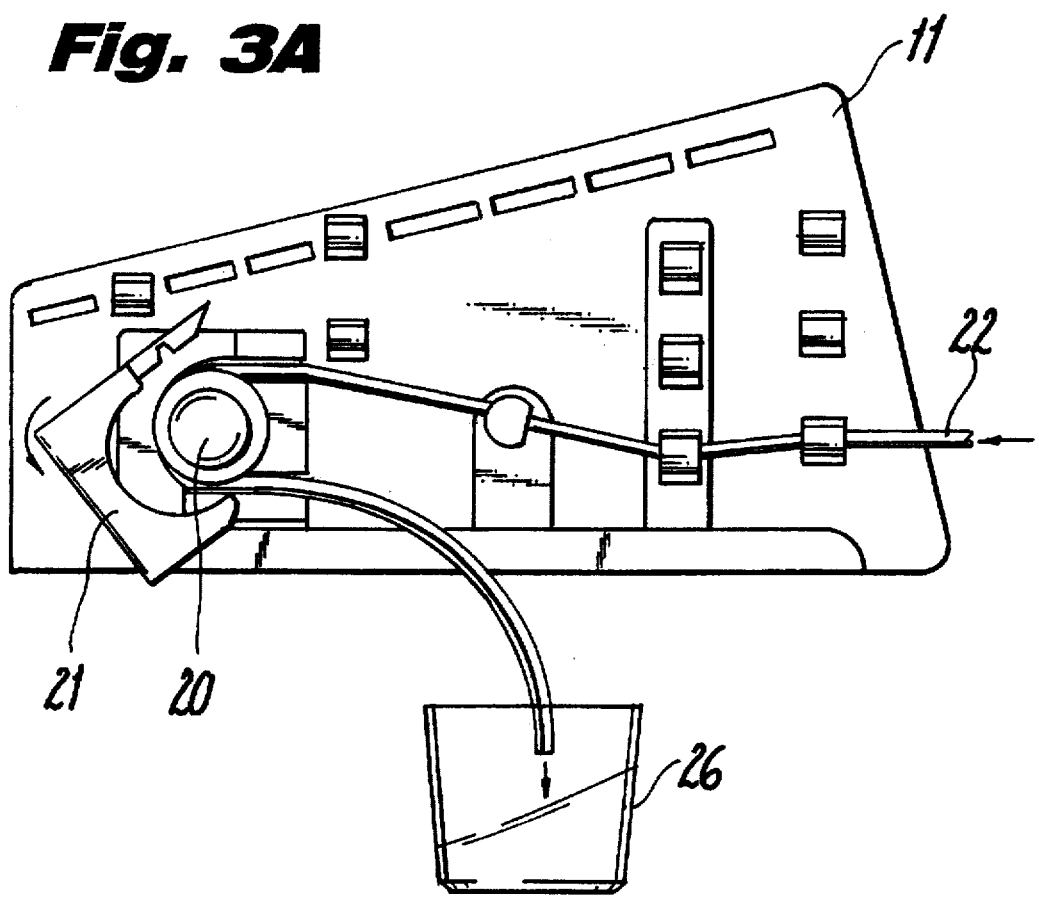
Figure 4A:
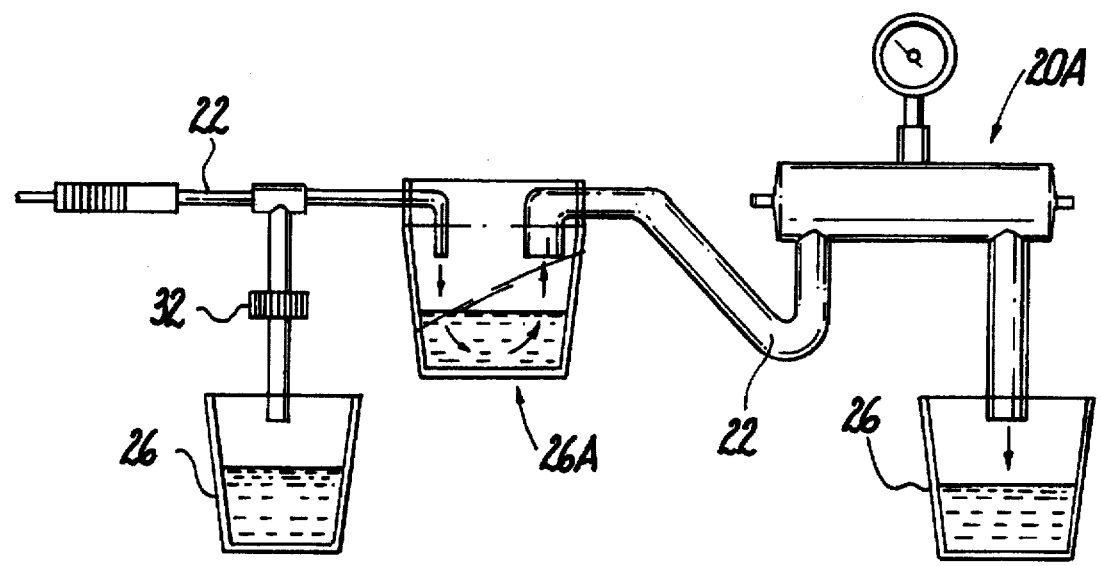
FIGS. 4A and 4B illustrate other possible modifications to conventional vacuum pumps in order to achieve automated free flow.
Figure 4B:
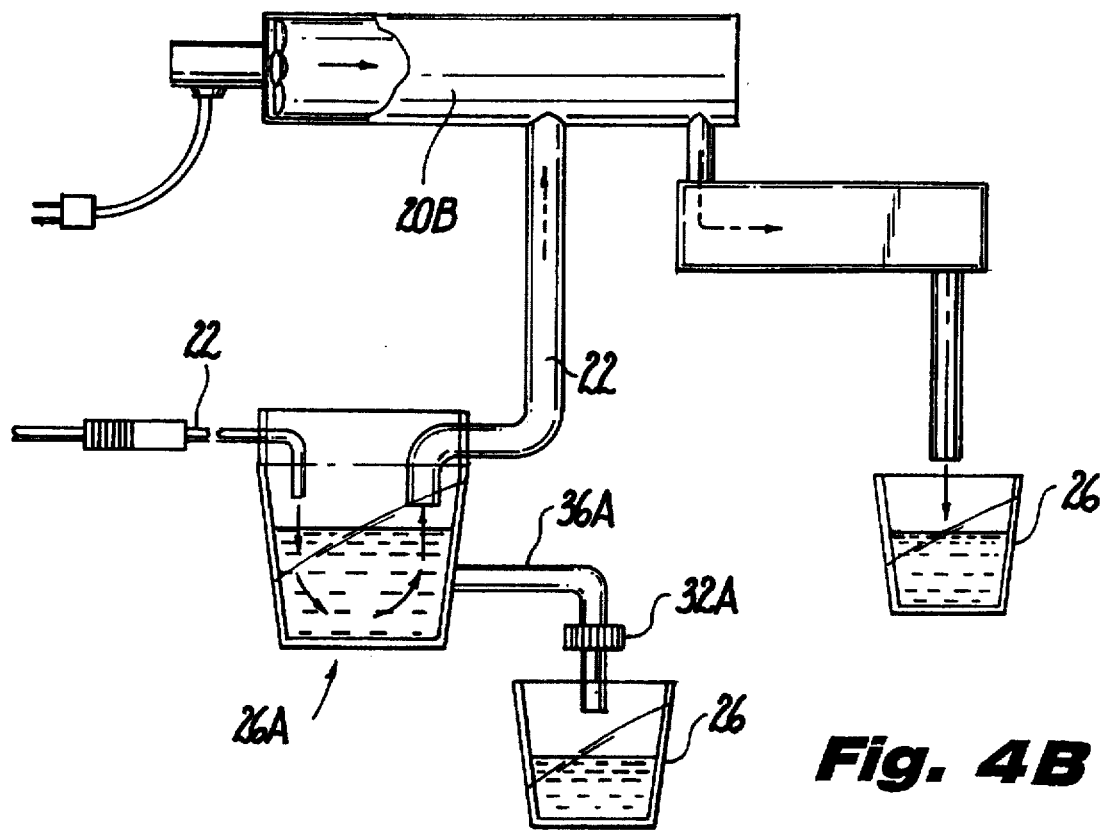

FIGS. 3 and 4 illustrate alternative methods for modifying existing phacoemulsification machines 10 to achieve the equivalent function of a free flow valve 32, provided that the infusion reservoir 12 is place at a higher position relative to the evacuation line 22. As shown in FIGS. 3 and 4, any mechanical disengagement of the vacuum pumps 20, 20A and 20B, which would approximate the automated free flow mechanism and allow for the free flow of fluid through the evacuation line 22. Therefore, such a modification is anticipated by the instant invention. For example, referring to FIGS. 3A and 3B, the peristaltic pump 20 would ordinarily have a pump cover 21 which presses the evacuation line 22 against the rollers of the pump. If this pump cover is opened (FIG. 3B), either manually or automatically, a free-flow state would be achieved. Alternatively, the diaphragm and venturi vacuum pumps (20A and 20B, respectively) illustrated in FIGS. 4A and 4B, may readily be modified to create a free flow condition by designing a valve to open the evacuation line 22 into a collection container 26. This may be done by inserting a "T" connector into the evacuation line 22 and diverting the fluid flow into a collection container 26A (FIG. 4A). Also, a free flow condition may be created by modifying the vacuum pump chamber to incorporate, for example, a valve to open up the vacuum pump chamber. Another method for modifying the phacoemulsification system using diaphragm or venturi pumps would be to introduce a free flow line 36A containing a free flow valve 32A into the enclosed collection container 26A. In this configuration, opening the free flow valve will effectively disengage the diaphragm and venturi pumps and establish the same free flow condition of fluid through the eye 50.

According to the invention, the free flow valve 32 may also be used to enhance surge prevention whenever the vacuum pump 20 is operating during the phacoemulsification, irrigation and aspiration process. When the vacuum in the evacuation line 22 exceeds a predetermined or preset vacuum limit, the pinch vent valve 42 will open for an instant, and then close again. By opening the vent valve 42, either atmospheric air or sterile fluid is allowed to flow into the evacuation line 22, thereby reducing the vacuum within the evacuation line 22 and/or the handpiece 14. The vacuum limit may be set directly on the phacoemulsification machine console 11. In machines unable to monitor vacuum levels in the evacuation line, venting may be initiated in various ways, for example, by the surgeon's foot pedal (not shown). In machines which employ a separate evacuation line valve (not shown), where the evacuation line valve is placed between the vent line and the free flow line, it may be desirable to have the free flow valve 32 open simultaneously with the vent valve 42. In this example, the evacuation line valve would be closed, thereby isolating the vacuum pump and the free flow line from the vent line and the eye.

Figure 6:
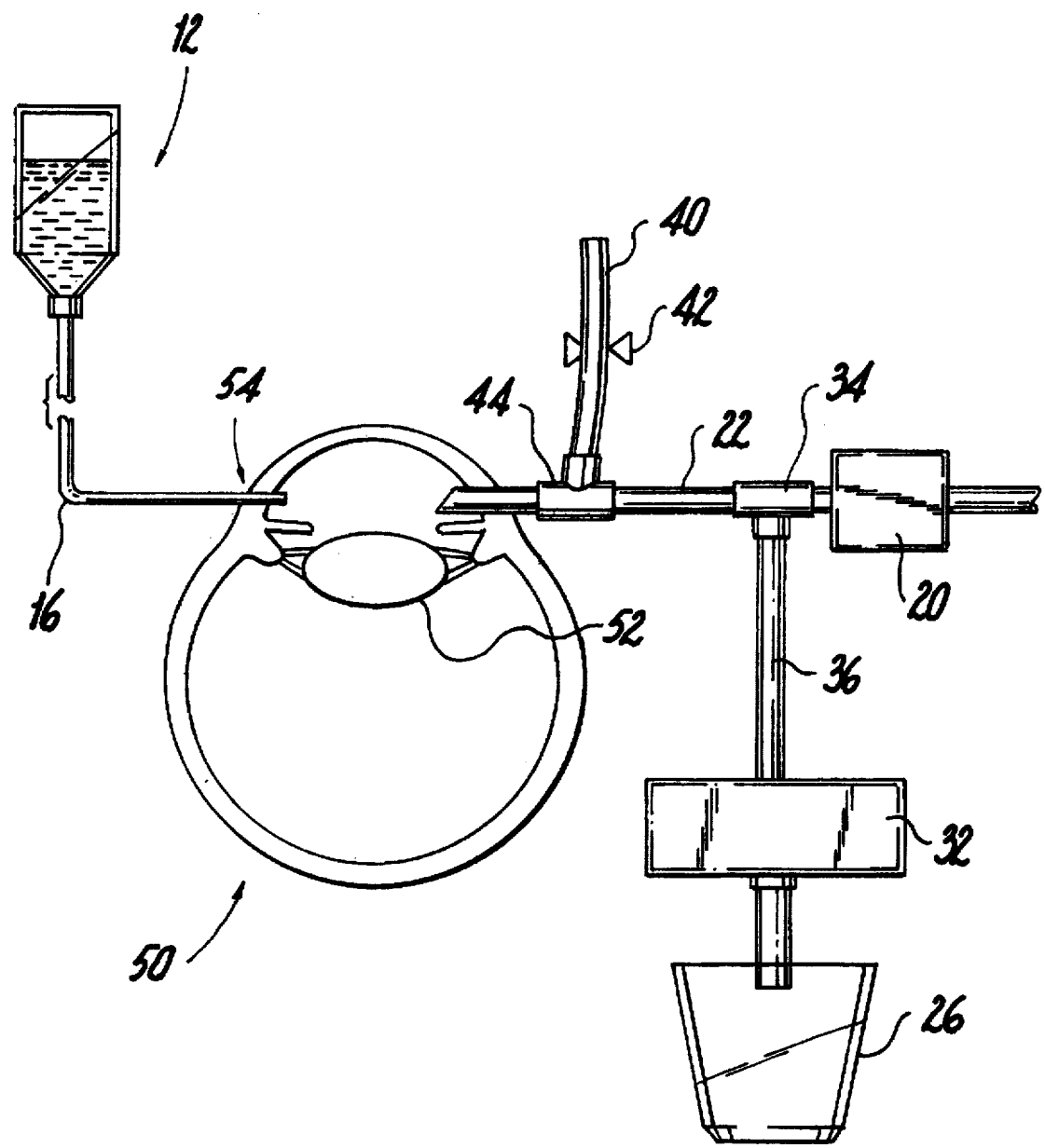
FIG. 6 illustrates a free flow valve used in the phacoemulsification process to provide enhanced surge protection.

Typically, venting mechanisms are not designed to permit fluid flow in the evacuation line 22. The vacuum pump 20 stops during venting and there is no fluid flow out of the either the venting or evacuation lines (40 or 22). According to the invention, however, the automated free flow mechanism uses the free flow valve 32 to allow fluid to flow through the evacuation line 22, in order to relieve the vacuum. As shown in FIG. 6, it is preferable to place the venting line 40 at a position close to the eye 50. This allows the proportion of fluid around the eye 50 to remain constant during the venting process. On the other hand, the free flow line 36 containing the free flow valve 32 may be placed in the vicinity of the vacuum pump 20. This increases the responsiveness of the free flow valve 32 during venting.

Further, because it may be preferable to use soft surgical tubing in the vicinity of the vacuum pump 20, by placing the free flow valve 32 close to the vacuum pump 20, the amount of soft tubing is minimized. This helps reduce surge from tube compression.

FIG. 7 illustrates an alternate embodiment of an AFF according to the present invention. This embodiment includes an infusion reservoir 12' that is placed at a higher level than the level of the eye 50' and an outlet 60 of a free flow line 36'. In addition, as illustrated in FIG. 7, the outlet 60 of the free flow line 36' is disposed above the level of the eye 50' by a predetermined distance A. In one embodiment distance A was about 4". Typically, the infusion reservoir 12 is disposed above the level of the eye by about two to three feet.

While the invention has been particularly shown and described with reference to preferred embodiments thereof, it will be understood by those skilled in the art that various changes in form and details may be made therein without departing from the spirit and scope of the invention.

I claim:

1. An apparatus for phacoemulsification, irrigation and aspiration for removing a cataract lens from an eye, said apparatus comprising:

an ultrasonic surgical handpiece for insertion into the eye;

an infusion reservoir containing infusion fluid, the infusion reservoir being connected to the ultrasonic surgical handpiece by an infusion line;

an evacuation line having a first end connected to the ultrasonic surgical handpiece and a second end which leads to a collection container;

a free flow valve, located along the evacuation line, for controlling the flow of fluid through the evacuation line, wherein the infusion reservoir is placed above the level of the eye and the level of an outlet of the evacuation line so that, when the free flow valve is in the open position, infusion fluid is permitted to flow from the infusion reservoir into the eye, through the evacuation line and into the collection container; and a third line having a first end connected to the evacuation line between the handpiece and the free flow valve.

2. The apparatus for phacoemulsification, irrigation and aspiration for removing a cataract lens from an eye as in claim 1, wherein said ultrasonic handpiece, when actuated, conveys fluid from within the eye into the evacuation line.

3. The apparatus for phacoemulsification, irrigation and aspiration for removing a cataract lens from an eye as in claim 2, wherein said ultrasonic handpiece includes a needle tip which has an internally stepped diameter.

4. The apparatus for phacoemulsification, irrigation and aspiration for removing a cataract lens from an eye as in claim 2, wherein said ultrasonic handpiece includes a needle tip that has a substantially constant internal diameter.

5. An apparatus for phacoemulsification, irrigation and aspiration for removing a cataract lens from an eye, said apparatus comprising:

a surgical handpiece for insertion into the eye;

an infusion reservoir containing infusion fluid, the infusion reservoir being connected to the surgical handpiece by an infusion line;

an evacuation line having a first end connected to the surgical handpiece and a second end which leads to a collection container;

a free flow valve, located along the evacuation line, for controlling the flow of fluid through the evacuation line, wherein the infusion reservoir is placed above the level of the eye and the level of an outlet of the evacuation line so that, when the free flow valve is in the open position, infusion fluid is permitted to flow from the infusion reservoir into the eye, through the evacuation line and into the collection container; and a third line having a first end connected to the evacuation line between the handpiece and the free flow valve.

6. The apparatus for phacoemulsification, irrigation and aspiration for removing a cataract lens from an eye as in claim 5, wherein a second end of the third line is connected to atmosphere.

7. The apparatus for phacoemulsification, irrigation and aspiration for removing a cataract lens from an eye as in claim 6, further including a valve disposed in said third line.

8. The apparatus for phacoemulsification, irrigation and aspiration for removing a cataract lens from an eye as in claim 5, wherein a second end of the third line is connected to a fluid reservoir.

9. The apparatus for phacoemulsification, irrigation and aspiration for removing a cataract lens from an eye as in claim 8, further including a valve disposed in said third line.

10. The apparatus for phacoemulsification, irrigation and aspiration for removing a cataract lens from an eye as in claim 8, wherein said fluid reservoir is disposed above said infusion reservoir.

11. The apparatus for phacoemulsification, irrigation and aspiration for removing a cataract lens from an eye, said apparatus comprising:

a surgical handpiece for insertion into the eye, the surgical handpiece having an evacuation port at a first end thereof;

an infusion reservoir containing infusion fluid, the infusion reservoir being connected to the surgical handpiece by an infusion line;

an infusion valve located along the infusion line in order to control the flow of infusion fluid through the infusion line;

a vacuum pump;

an evacuation line having a first end connected to the surgical handpiece at the evacuation port, and a second end connected through the vacuum pump and leading into a collection container;

a free flow line connected at one end to the evacuation line at a location between the surgical handpiece and the vacuum pump, the other end of the free flow line being directed into the collection container;

a free flow valve, located along the free flow line, for controlling the flow of fluid through the free flow line, wherein the infusion reservoir is placed above the level of the eye and the level of an outlet of the evacuation line so that, when the free flow valve is in the open position, infusion fluid is permitted to flow from the infusion reservoir into the eye, through the evacuation line, through the free flow line, and into the collection container.

12. The apparatus for phacoemulsification, irrigation and aspiration for removing a cataract lens from an eye as in claim 11, wherein the infusion, evacuation, and free flow lines are made from surgical tubing.

13. The apparatus for phacoemulsification, irrigation and aspiration for removing a cataract lens from an eye as in claim 11, wherein the vacuum pump is a peristaltic pump.

14. The apparatus for phacoemulsification, irrigation and aspiration for removing a cataract lens from an eye as in claim 11, wherein the vacuum pump is a diaphragm pump.

15. The apparatus for phacoemulsification, irrigation and aspiration for removing a cataract lens from an eye as in claim 11, wherein the vacuum pump is a venturi pump.

16. The apparatus for phacoemulsification, irrigation and aspiration for removing a cataract lens from an eye as in claim 11, wherein the infusion valve is a mechanical pinch valve.

17. The apparatus for phacoemulsification, irrigation and aspiration for removing a cataract lens from an eye as in claim 11, wherein the infusion valve is a solenoid-operated pinch valve.

18. The apparatus for phacoemulsification, irrigation and aspiration for removing a cataract lens from an eye as in claim 13, wherein the free flow valve is a mechanical pinch valve.

19. The apparatus for phacoemulsification, irrigation and aspiration for removing a cataract lens from an eye as in claim 13, wherein the free flow valve is a solenoid-operated pinch valve.

20. The apparatus for phacoemulsification, irrigation and aspiration for removing a cataract lens from an eye as in claim 11, wherein the free flow line is connected to the evacuation line by a "T" connector.

21. An apparatus for phacoemulsification, irrigation and aspiration for removing a cataract lens from an eye, said apparatus comprising:

an ultrasonic handpiece for insertion into the eye, the ultrasonic handpiece having a first evacuation port at a first end thereof, and further providing means for emulsifying the cataract lens;

an irrigation and aspiration handpiece for insertion into the eye after the cataract lens has been emulsified, the irrigation and aspiration handpiece having a second evacuation port at a first end thereof;

an infusion reservoir containing infusion fluid, the infusion reservoir being connected to one of the ultrasonic handpiece and the irrigation and aspiration handpiece by an infusion line;

an infusion valve located along the infusion line in order to control the flow of infusion fluid through the infusion line;

a vacuum pump;

an evacuation line having a first end connected to one of the ultrasonic handpiece and the irrigation and aspiration handpiece at the corresponding evacuation port, and a second end connected through the vacuum pump and leading into a collection container;

a free flow line connected at one end to the evacuation line at a location between the surgical handpiece and the vacuum pump, the other end of the free flow line being directed into the collection container;

a free flow valve, located along the free flow line, for controlling the flow of fluid through the free flow line, wherein, the infusion reservoir is placed above the level of the eye and the level of an outlet of the evacuation line so that, when the free flow valve is in the open position, infusion fluid is permitted to flow from the infusion reservoir into the eye, through the evacuation line, through the free flow line, and into the collection container.

22. The apparatus for phacoemulsification, irrigation and aspiration for removing a cataract lens from an eye as in claim 21, wherein the infusion, evacuation, and free flow lines are made from surgical tubing.

23. The apparatus for phacoemulsification, irrigation and aspiration for removing a cataract lens from an eye as in claim 21, wherein the vacuum pump is a peristaltic pump.

24. The apparatus for phacoemulsification, irrigation and aspiration for removing a cataract lens from an eye as in claim 21, wherein the vacuum pump is a diaphragm pump.

25. The apparatus for phacoemulsification, irrigation and aspiration for removing a cataract lens from an eye as in claim 21, wherein the vacuum pump is a venturi pump.

26. The apparatus for phacoemulsification, irrigation and aspiration for removing a cataract lens from an eye as in claim 21, wherein the infusion valve is a mechanical pinch valve.

27. The apparatus for phacoemulsification, irrigation and aspiration for removing a cataract lens from an eye as in claim 21, wherein the infusion valve is a solenoid-operated pinch valve.

28. The apparatus for phacoemulsification, irrigation and aspiration for removing a cataract lens from an eye as in claim 21, wherein the free flow valve is a mechanical pinch valve.

29. The apparatus for phacoemulsification, irrigation and aspiration for removing a cataract lens from an eye as in claim 21, wherein the free flow valve is a solenoid-operated pinch valve.

30. The apparatus for phacoemulsification, irrigation and aspiration for removing a cataract lens from an eye as in claim 21, wherein the free flow line is connected to the evacuation line by a "T" connector.

31. The apparatus for phacoemulsification, irrigation and aspiration for removing a cataract lens from an eye as in claim 21, further comprising:

a venting fluid reservoir containing venting fluid, the venting fluid reservoir being connected to the evacuation line via a venting line; and a vent valve located on the venting line to control the flow of venting fluid therethrough.

32. The apparatus for phacoemulsification, irrigation and aspiration for removing a cataract lens from an eye as in claim 31, wherein the venting valve is a mechanically operated pinch valve.

33. The apparatus for phacoemulsification, irrigation and aspiration for removing a cataract lens from an eye as in claim 31, wherein the venting valve is a solenoid-operated pinch valve.

34. The apparatus for phacoemulsification, irrigation and aspiration for removing a cataract lens from an eye as in claim 31, wherein the venting line is connected to the evacuation line by a "T" connector.

35. The apparatus for phacoemulsification, irrigation and aspiration for removing a cataract lens from an eye as in claim 21, further comprising:

a vent line, connected to the evacuation line at a first end, the other end being open to the atmosphere; and a vent valve located on the venting line to control the passage of air therethrough.

36. The apparatus for phacoemulsification, irrigation and aspiration for removing a cataract lens from an eye as in claim 35, wherein the venting valve is a mechanically operated pinch valve.

37. The apparatus for phacoemulsification, irrigation and aspiration for removing a cataract lens from an eye as in claim 35, wherein the venting valve is a solenoid-operated pinch valve.

38. The apparatus for phacoemulsification, irrigation and aspiration for removing a cataract lens from an eye as in claim 35, wherein the venting line is connected to the evacuation line by a "T" connector.

39. A method for removing particles from the surface of the lens using a phacoemulsification machine, comprising the steps of:

inserting a handpiece, capable of phacoemulsification, irrigation and aspiration into an eye, the handpiece being attached to an infusion reservoir via an infusion line, the handpiece further being attached to a vacuum pump via an evacuation line;

placing the infusion reservoir containing infusion fluid above the level of both the eye and an outer of the evacuation line;

opening an infusion line valve located along the infusion line to control the flow in infusion fluid therethrough;

opening a free flow valve located along the evacuation line between the eye and the vacuum pump, so that relative higher position of the infusion reservoir with respect to the evacuation line causes infusion fluid to flow from the infusion reservoir, through the eye and through the evacuation line.

40. The method for removing particles from the surface of the lens using a phacoemulsification machine as described in claim 39, further comprising the steps of:

shutting down the vacuum pump before the free flow valve is opened; and collecting the infusion fluid in a collection container as it passes through the evacuation line.

41. A method for removing particles from the surface of the lens using a phacoemulsification machine, comprising the steps of:

inserting a handpiece, capable of phacoemulsification, irrigation and aspiration into an eye, the handpiece being attached to an infusion reservoir via an infusion line, the handpiece further being attached to a vacuum pump via an evacuation line;

placing the infusion reservoir containing infusion fluid above the level of both the eye and an outlet of the evacuation line;

moving a surgeon controlled foot switch located on the phacoemulsification machine into a first position in order to (1) open an infusion line valve located along the infusion line to control the flow in infusion fluid therethrough, (2) close a vent valve located along a venting line, the venting line being attached to a venting fluid reservoir, (3) close a free flow valve located along the evacuation line between the eye and the vacuum pump, and (4) turn the vacuum pump to off;

moving the surgeon controlled foot switch to a second position in order to open the free flow valve, so that relative higher position of the infusion reservoir with respect to the evacuation line causes infusion fluid to flow from the infusion reservoir, through the eye and through the evacuation line;

maneuvering the handpiece across the surface of the lens to remove the lens particles therefrom.

42. The method for removing particles from the surface of the lens using a phacoemulsification machine as described in claim 41, further comprising the steps of:

placing the venting fluid reservoir at a higher location relative to the infusion reservoir;

moving the surgeon controlled foot switch back to the first position in order to open the vent valve, thereby causing a reverse pressure differential which halts the fluid flow through the eye.

43. The method for removing particles from the surface of the lens using a phacoemulsification machine as described in claim 42, further comprising the step of:

moving the surgeon controlled foot switch to third position in order to activate the vacuum pump and close the free flow valve, thereby creating vacuum pressure to draw fluid through the eye.

44. The method for removing particles from the surface of the lens using a phacoemulsification machine as described in claim 42, wherein placing the surgeon controlled foot switch in one of a first, second and third position, produces a different audible signal corresponding to each surgeon controlled foot switch position.

45. An apparatus for removing particles from the surface of a lens within an eye using a phacoemulsification machine, said apparatus comprising:

a surgical handpiece for insertion into the eye, the surgical handpiece having an evacuation port at a first end thereof, and further providing means for phacoemulsification, irrigation and aspiration of the lens from within the eye;

an infusion reservoir containing infusion fluid, the infusion reservoir being connected to the surgical handpiece by an infusion line;

an infusion valve located along the infusion line in order to control the flow of infusion fluid through the infusion line;

a peristaltic vacuum pump;

an evacuation line having a first end connected to the surgical handpiece at the evacuation port, and a second end connected through the peristaltic vacuum pump and leading into a collection container, wherein infusion fluid is permitted to flow from the infusion reservoir into the eye, through the evacuation line, through the free flow line, and into the collection container, by (1) placing the infusion reservoir above the level of the eye and the level of an outlet of the evacuation line, (2) opening the infusion valve, and (3) disengaging the peristaltic pump.

46. An apparatus for removing particles from the surface of a lens within an eye using a phacoemulsification machine, said apparatus comprising:

a surgical handpiece for insertion into the eye, the surgical handpiece having an evacuation port at a first end thereof, and further providing means for phacoemulsification, irrigation and aspiration of the lens from within the eye;

an infusion reservoir containing infusion fluid, the infusion reservoir being connected to the surgical handpiece by an infusion line;

an evacuation line having a first end connected to the surgical handpiece at the evacuation port, and a second end leading into an enclosed collection jar;

a diaphragm vacuum pump having one end attached to the enclosed collection jar, so that when the diaphragm vacuum pump is activated a vacuum is created, thereby drawing fluid through the evacuation line and into the collection jar; and a free flow line connected to the enclosed collection jar, the free flow line containing a free flow valve, wherein fluid is permitted to flow from the infusion reservoir into the eye, through the evacuation line, through the free flow line, and into the collection container, by (1) placing the infusion reservoir above the level of the eye and the level of an outlet of the evacuation line, (2) opening the infusion valve, and (3) opening the free flow valve which effectively disengages the diaphragm pump.

47. An apparatus for removing particles from the surface of a lens within an eye using a phacoemulsification machine, said apparatus comprising:

a surgical handpiece for insertion into the eye, the surgical handpiece having an evacuation port at a first end thereof, and further, the surgical handpiece providing means for phacoemulsification, irrigation and aspiration of the lens from within the eye;

an infusion reservoir containing infusion fluid, the infusion reservoir being connected to the surgical handpiece by an infusion line;

an evacuation line having a first end connected to the surgical handpiece at the evacuation port, and a second end leading into an enclosed collection jar;

a venturi vacuum pump having one end attached to the enclosed collection jar, so that when the diaphragm vacuum pump is activated a vacuum is created, thereby drawing fluid through the evacuation line and into the collection jar; and a free flow line connected to the enclosed collection jar, the free flow line containing a free flow valve, wherein fluid is permitted to flow from the infusion reservoir into the eye, through the evacuation line, through the free flow line, and into the collection container, by (1) placing the infusion reservoir above the level of the eye and the level of an outlet of the evacuation line, (2) opening the infusion valve, and (3) opening the free flow valve which effectively disengages the venturi pump.

48. An apparatus for phacoemulsification, irrigation and aspiration for removing a cataract lens from an eye, said apparatus comprising:

a surgical handpiece for insertion into the eye;

an infusion reservoir containing infusion fluid, the infusion reservoir being connected to the surgical handpiece by an infusion line;

an evacuation line having a first end connected to the surgical handpiece and a second end which leads to a collection container;

a free flow valve, located along the evacuation line, for controlling the flow of fluid through the evacuation line, wherein the infusion reservoir is placed above the level of the eye and the level of an outlet of the evacuation line, the outlet of the evacuation line is placed above the level of the eye so that, when the free flow valve is in the open position, infusion fluid is permitted to flow from the infusion reservoir into the eye, through the evacuation line and into the collection container; and a valve connecting member for connecting at least a third line between the handpiece and the free flow valve.

* * * * *